US00PP31711P2

(12) United States Plant Patent
Zary

(10) Patent No.: US PP31,711 P2
(45) Date of Patent: May 5, 2020

(54) ROSE PLANT NAMED 'ZARREFRE'

(50) Latin Name: *Rosa hybrida*
Varietal Denomination: ZARrefre

(71) Applicant: Gardens Alive! Inc., Greendale, IN (US)

(72) Inventor: Keith W. Zary, Missoula, MT (US)

(73) Assignee: Gardens Alive! Inc., Greendale, IN (US)

( * ) Notice: Subject to any disclaimer, the term of this patent is extended or adjusted under 35 U.S.C. 154(b) by 0 days.

(21) Appl. No.: 16/501,781

(22) Filed: Jun. 3, 2019

(51) Int. Cl.
*A01H 5/02* (2018.01)
*A01H 6/74* (2018.01)

(52) U.S. Cl.
USPC ..... Plt./108

(58) Field of Classification Search
USPC ..... Plt./108
CPC ..... A01H 5/02; A01H 6/74
See application file for complete search history.

*Primary Examiner* — Annette H Para
(74) *Attorney, Agent, or Firm* — Barbara Campbell; Cochran Freund & Young LLC

(57) ABSTRACT

A new and distinct variety of shrub rose having a compact and upright growth habit, suitable for outdoor garden decoration, bright red flowers borne in clusters and singly, and dark-green, glossy foliage, is disclosed.

1 Drawing Sheet

Genus and species: *Rosa hybrida.*
Denomination: 'ZARrefre'.

BACKGROUND

'ZARrefre' is a new and distinct variety of shrub rose. 'ZARrefre' originated from a controlled hybridization in May to June 2011 in Miami, Ohio between the female parent, and un-named and unpatented pink shrub rose seedling, and the male parent, 'RADrazz' (U.S. Plant Pat. No. 11,836).

The resulting seeds from the hybridization were planted and evaluated. 'ZARrefre' was selected in July 2012 in a greenhouse in Miami, Ohio. 'ZARrefre' was first asexually propagated in August 2012 in Miami, Ohio on its own root cuttings and in June 2013 by budding and grafting on the plant/rootstock of *Rosa hybrida* 'Dr. Huey' (unpatented) in Kern County, Calif.

Other subsequent asexual propagations were conducted in controlled environments in Kern County, Calif. and Tipp City, Ohio and demonstrate that 'ZARrefre' reproduces true to type in successive generations of asexual reproduction via softwood cuttings, budding, and grafting.

SUMMARY

The following are the most outstanding and distinguishing characteristics of this new variety when grown under normal horticultural practices in Kern County, Calif. and Tipp City, Ohio.

1. A shrub rose having a compact and upright growth habit, suitable for outdoor garden decoration;
2. Bright red flowers borne in clusters and singly; and
3. Dark-green, glossy foliage.

DESCRIPTION OF THE PHOTOGRAPH

This rose plant is illustrated by the accompanying photograph which shows the individual parts of the plant. The colors shown are as true as can be reasonably obtained by conventional photographic procedures. The photograph is of the parts of a 3 to 4-year old rose plant grown outdoors in Tipp City, Ohio in August 2018. The colors shown are as true as can be reasonably obtained by conventional photographic procedures.

The photograph shows from top to bottom, starting at the top (first) row from left to right, three individual flowers in full bloom, from the older full bloom to newer full bloom and the reproductive parts of the flower with the petals removed; the second row shows from left to right an older flowering stem with multiple buds and an immature flowering stem with multiple buds and foliage; the third row shows from left to right, the upper surface of the compound leaf, and the lower surface of the compound leaf; and the fourth row shows an individual immature stem with thorns and anthocyanin coloration; and the fifth row (bottom) row shows an individual stem with only thorns of the plant.

DETAILED DESCRIPTION

The following detailed descriptions set for the distinctive characteristics of 'ZARrefre'. The data which define these characteristics were collected outdoors in Tipp City, Ohio in August 2018 from 3 to 4-year old plants. The phenotype of this new variety will vary somewhat with variation in environmental, climatic, and cultural conditions as it has not been tested in other environments. Color references are to The R.H.S. Colour Chart of The Royal Horticultural Society of London (R.H.S.) 2001.

Classification:
*Family.*—Rosaceae.
*Species.*—*Rosa hybrida.*
*Common name.*—Shrub rose.
*Variety.*—'ZARrefre'.

Parentage:
*Female parent.*—An un-named and unpatented rose plant.
*Male parent.*—RADrazz' (U.S. Plant Pat. No. 11,836).

Growth: The plant has a bushy upright growth habit, about 120 cm to about 150 cm in height and about 90 cm to about 110 cm spread at the widest point, with full branching. It displays vigorous growth and the canes are of medium caliper for the class, about 5 mm to about 6 mm in diameter at the widest point.

Stems: The color of the major stems is near RHS 146A. The major stems are rough in texture and they bear several large prickles that are about 7 mm to about 8 mm in length. The large prickles are hooked downward with a medium length base; prickle color is near RHS 176B. The major stem bears few if any small prickles. There are no fine or coarse hairs on major stems. The color of the side branches is near RHS 146B with an overlay of RHS 176A. The branches are rough in texture and they bear several large prickles which are of a similar size and shape to the large prickles on the major stems; prickle color is between RHS 183B and RHS 183C. The branches bear no small prickles. There are no fine or coarse hairs on side branches. The color of the new shoots is between RHS 183A and RHS 183B but quickly becomes green. The new shoots are rough in texture and they bear several many large prickles which are of similar size and shape to the large prickles on the major stems; prickle color is near RHS 183A. The shoots bear no small prickles. There are no fine or coarse hairs on new shoots.

Foliage: The compound leaves are usually comprised of three to seven leaflets and are borne abundantly in normal quantities. The five-leaflet leaves are about 9 cm to about 10.5 cm in length and about 6.5 cm to about 7.5 cm in width at the widest point, very leathery in texture on both sides, and glossy in finish on the upper side and matte in finish on the underside. The leaves have a pinnate venation pattern. The terminal leaflets are about 4.0 cm to about 4.5 cm in length and about 3.0 cm to about 3.2 cm in width at the widest point, shaped oval to ovate with acute apices and round bases. Their margins are serrate. The upper and lower surface color of the mature leaf is near between RHS 139A and RHS 147B. The lower surface color of the mature leaf is near RHS 147B. The lower and upper surface colors of the leaf veins on the mature leaf are similar in coloration to the upper and lower surfaces colors of the mature leaf. The upper and lower surface colors of the young leaf is RHS 178A. The lower surface color of the young leaf is near RHS 178A. The lower and upper surface colors of the leaf veins on the young leaf are similar in coloration to the upper and lower surfaces colors of the young leaf. The rachis is about 5.5 cm to about 6.0 cm in length, about 2 mm in width at the widest point, and moderately rough. The upper surface is shallowly grooved with some many stipitate glands on the edges of the grooves. The lower surface of the rachis is rough with small prickles. The rachis color is near RHS 147C on the lower surface and near RHS 147B on the upper surface, often with areas right along the middle of the rachis in RHS 147D. The stipules are about 1.0 cm to about 1.2 cm in length and of medium width, about 0.4 cm, with medium straight points that usually turn out at an angle of less than 45 degrees. The lower and upper surface color of the stipule is between RHS 147C and RHS 147B. The upper and lower surfaces of the stipules are smooth in texture. The petiole is average in caliper and somewhat smooth. The upper surface is shallowly grooved with a few stipitate glands on the edges of the grooves. The lower surface of the petiole is smooth. The petiole is about 2 mm to about 3 mm in length and about 1 mm in width at the widest point. The petiole color is near RHS 147C on the lower surface and near RHS 147B on the upper surface, sometimes often lightly moderately heavily suffused on the young leaves with near RHS 176B.

Flower: 'ZARrefre' usually bears its flowers singly and in clusters of three to five or more per stem. Flowers are may be borne in rounded to pyramidal clusters on strong medium length stems, about 35 cm to about 45 cm. The cluster ranges from about 11 cm to about 14 cm in diameter. Outdoors, the plant blooms abundantly and nearly continuously during the growing season. The flowers have no a slight spicy fragrance.

Flower bud: Before the calyx breaks, the bud is about 1.0 cm to about 1.3 cm in diameter at the widest point, about 2.0 cm to about 2.3 cm in length, pointed to ovoid in shape with a conspicuous neck. The surface of the bud bears between 5 to 10 or more foliaceous appendages, usually with foliaceous parts extending beyond the tip of the bud about ¼ or more of its length. Bud color is near RHS 138B sometimes heavily suffused, especially on the side exposed to the sun, with near RHS 175A. As the petals open (after the calyx breaks), the bud is about 1.5 cm to about 1.7 cm in diameter at the widest point, about 2.5 cm to about 2.7 cm in length, and somewhat pointed to ovoid in form. The color of the lower and upper surfaces of the newly opened petals is near between RHS N66B and RHS 45A. At the point where the petal attaches, there is a small zone of near RHS N155B.

Petals and petaloids: The substance of the petals is leathery crisp and of thick thickness, with upper surfaces somewhat satiny to velvety and under surfaces satiny to velvety. The petals are about 3.5 cm to about 3.7 cm in length and about 3.3 cm to about 3.5 cm in width at the widest point. Petal margins are entire. The outer petals are ovate to orbicular in shape with apices rounded and sometimes slightly notched with one notch. The inner petals are ovate to obdeltoid to lanceolate in shape with apices rounded and slightly notched with one notch. Petaloids are about 1.0 cm to about 2.0 cm in length and about 0.5 cm to about 1.0 cm in width at the widest point. Petaloids are shaped oblong to subulate with rounded to muticous apices.

Sepals: The sepals are 5 per flower, about 1.7 cm to about 1.8 cm in length and about 0.7 cm to about 0.8 cm in width at the widest point. The outer surface color of the sepal is near RHS 138B and often lightly suffused, especially on the side exposed to the sun, with RHS 175A to RHS 175B. The outer surface of the sepal is smooth bears between 5 to 10 or more foliaceous appendages with some stipitate glands. The inner surface color of the sepal is near RHS 138C broadly bordered by near RHS 155C. After the sepals open, the inner surface color is sometimes lightly suffused, especially on the area exposed to the sun, with RHS 175B. The inner surface of the sepal is covered and edged with fine wooly tomentum; sepal margins are entire and without stipulate glands. The sepals are somewhat permanent, and usually spear-shaped to recurved in shape with acute apices. The receptacle of the flower is of medium length, about 1.0 cm to 1.1 cm, and of average caliper, 0.9 cm to about 1.0 cm in diameter. The receptacle is somewhat ovoid to oblong to globular in form. Its surface is very smooth with thick fleshy walls. The receptacle color is near RHS 146A.

Peduncle: The peduncle is about 5 cm to about 6 cm in length, of average to caliper, about 2 mm to about 3 mm in diameter, and usually erect and stiff. It is rough, with numerous stipitate glands and prickles. Peduncle color is near RHS 138B sometimes lightly suffused, especially on the side exposed to the sun, with near RHS 175A to RHS 175B.

Newly open flower: The lower and upper surface color of the outer petals is between RHS N66B and RHS 45A. At the point where the petal attaches, there is a small large zone of near RHS N155B. The upper surface color of the outer petals is between 45A and 45B. At the point where the petal attaches, there is a small zone of RHS N155B. The lower and upper surface color of the intermediate petals is between RHS N66B and RHS 45B. The upper surface color of the intermediate petals is near RHS 45B. The lower and upper surface color of the inner petals is between RHS N66B and RHS 45B. The upper surface color of the inner petals is near RHS 45B. The lower and upper surface colors of the petaloids are similar in coloration to the upper and lower surfaces of the intermediate and inner petals. The general tonality of the newly opened flower is RHS 45B.

Three-day-old flower: The lower and upper surface color of the outer petals is near RHS N66A to RHS N66B. At the point where the petal attaches, there is a small zone of near RHS N155B. The upper surface color of the outer petals is between RHS N66A. At the point where the petal attaches, there is a small zone of near RHS N155B. The lower and upper surface color of the inner petals is between RHS N66A to RHS N66B. The upper surface color of the inner petals is near RHS N66A to RHS N66B. The lower and upper surface colors of the petaloids are similar in coloration to the upper and lower surfaces of the intermediate and inner petals. The general tonality of the three-day-old flower is near RHS N66B. On the spent bloom, the petals and petaloids drop off cleanly. In August in Tipp City, Ohio blooms on the bush growing outdoors generally last about four to five days. Cut roses from plants grown outdoors and kept at normal indoor living temperatures generally last about four to five days.

Fully-open flower: When fully open, the bloom ranges from about 7 cm to about 8 cm in diameter. Petalage is semi-double with about 15 to 20 petals and about 0 to 3 petaloids irregularly arranged. When partially open, the bloom form is high centered, and the petals are spiraled with petal edges somewhat reflexed. When fully open, the bloom form is flat, and the petals are imbricated with petal edges reflexed inward.

Hips and seed formation: Hips have not been observed on this variety when grown in Tipp City, Ohio.

Male reproductive organs: Stamens are average to many in number, average about 65, and are arranged regularly about the pistils; a few are mixed with petaloids or tucked in the calyx. The filaments are of medium length, about 7 mm to about 9 mm, most with anthers. Filaments are near RHS 62B in color. The anthers are medium for the class and all open approximately at the same time. Anther color when immature is near RHS 159A on the external part and near RHS 66B on the internal part. Anther color at maturity is near RHS 164B on the external part and near RHS 165B on the internal part. Pollen is somewhat sparse and near RHS 164C in color.

Female reproductive organs: Pistils vary in number, average about 25. The styles are even, average in length, about 5 mm to about 7 mm, average in caliper, and columnar. Stigma color is near RHS N159D. Style color is near RHS 46B. Ovaries are enclosed in the calyx. The ovaries are of medium size and are near RHS 155B in color.

Disease resistance: The plant displays an above average degree of resistance to powdery mildew (*Sphaerotheca pannosa*), downy mildew (*Peronospora sparsa*), black spot (*Diplocarpon rosae*) and rust (*Phragmidium* sp.) as compared to other commercial varieties grown under comparable conditions in Tipp City, Ohio. The plant's winter hardiness has been determined in Tipp City where it has survived typical Zone 5b cold to −16 degrees Fahrenheit without snow cover and without any additional winter protection. Drought/heat tolerance are yet to be determined.

COMPARISON WITH PARENTAL AND COMMERCIAL LINES

'ZARrefre' may be distinguished from the female parent, an un-named shrub rose plant by the following combination of characteristics: the female parent has bright pink flowers, while 'ZARrefre' has bright red flowers. The female parent has 10 cm to 12 cm diameter flowers, while 'ZARrefre' has 7 cm to 8 cm diameter flowers. The female parent has quite dull matte foliage when compared to the dark green glossy foliage of 'ZARrefre'.

'ZARrefre' may be distinguished from the male parent, RADrazz' by the following combination of characteristics: 'RADrazz' has matte green foliage, while 'ZARrefre' has very deep green glossy foliage. The male parent also has 5 to 7 petals, while 'ZARrefre' has 15 to 20 petals.

'ZARrefre' may be distinguished from its closest commercially available cultivar, 'RADrazz' (U.S. Plant Pat. No. 11,836) by the following combination of characteristics: 'RADrazz' has quite dull matte foliage compared to the bright glossy green foliage of 'ZARrefre'. 'RADrazz' has 5 to 7 petals, while 'ZARrefre' has 15 to 20 petals. 'ZARrefre' is also considerably larger than 'RADrazz' plant (120 cm to 150 cm tall versus 90 cm to 110 cm tall).

I claim:

1. A new and distinct variety of rose plant designated 'ZARrefre' as illustrated and described herein.

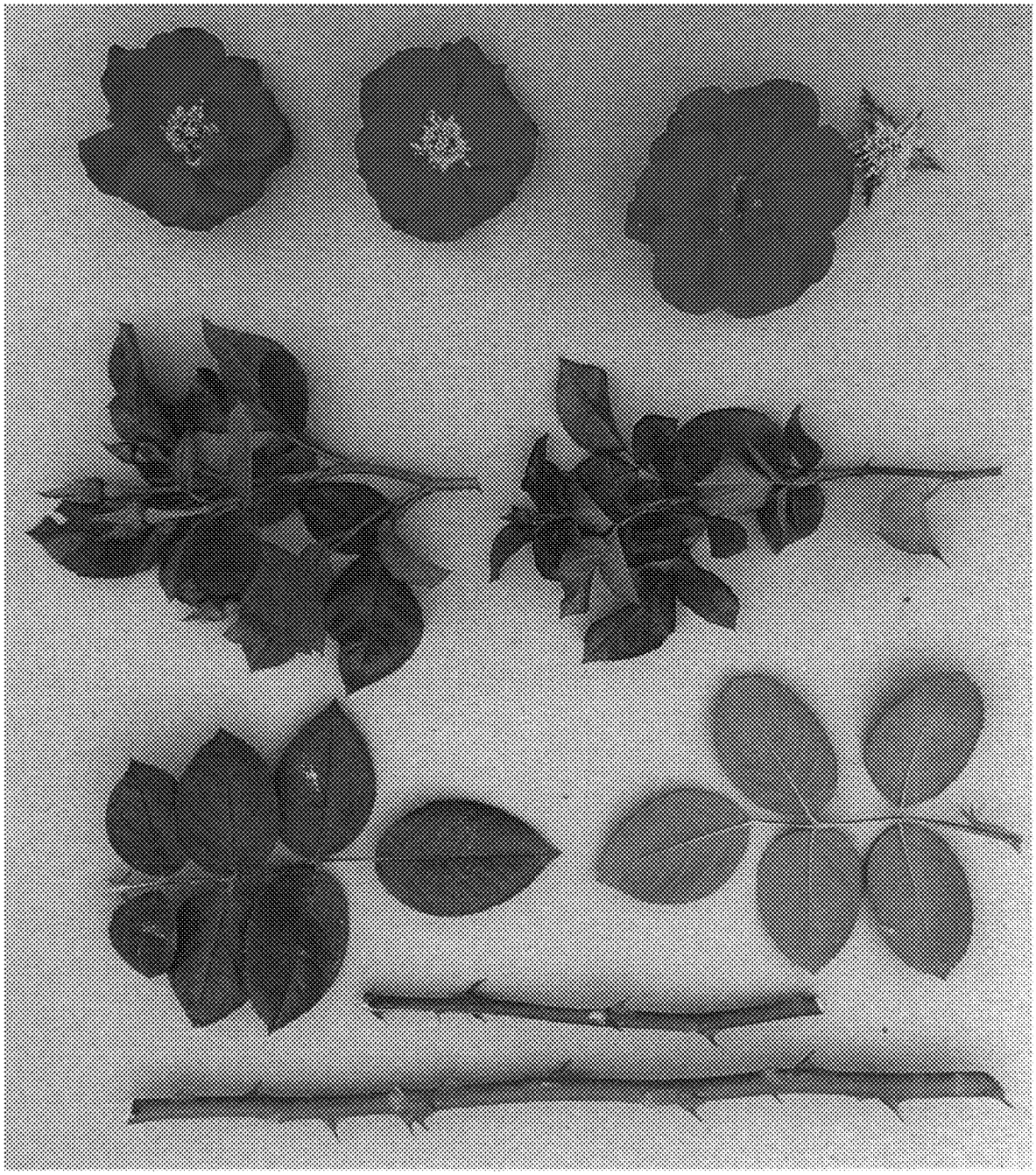

* * * * *